(12) United States Patent
Xiao et al.

(10) Patent No.: US 10,390,692 B2
(45) Date of Patent: Aug. 27, 2019

(54) HYBRID DETECTION APPARATUS

(71) Applicant: HTC Corporation, Taoyuan (TW)

(72) Inventors: Bo-Wen Xiao, Taoyuan (TW); Ming-Tien Lin, Taoyuan (TW); Chih-Jen Hu, Taoyuan (TW)

(73) Assignee: HTC Corporation, Taoyuan (TW)

( * ) Notice: Subject to any disclaimer, the term of this patent is extended or adjusted under 35 U.S.C. 154(b) by 768 days.

(21) Appl. No.: 14/951,487

(22) Filed: Nov. 25, 2015

(65) Prior Publication Data
US 2017/0143198 A1     May 25, 2017

(51) Int. Cl.
*A61B 1/227*     (2006.01)
*A61B 1/00*     (2006.01)
(Continued)

(52) U.S. Cl.
CPC ............ *A61B 1/227* (2013.01); *A61B 1/0002* (2013.01); *A61B 1/0005* (2013.01); *A61B 1/00006* (2013.01); *A61B 1/00009* (2013.01); *A61B 1/00016* (2013.01); *A61B 1/00027* (2013.01); *A61B 1/00032* (2013.01); *A61B 1/00108* (2013.01); *A61B 1/00163* (2013.01);
(Continued)

(58) Field of Classification Search
CPC ........ G01K 13/002; A61B 1/227; A61B 1/07; A61B 1/0002; A61B 1/00027; A61B 1/00163; A61B 1/05; A61B 1/055; A61B 5/6817; A61B 1/233; A61B 1/247; A61B 5/0077; A61B 5/01; A61B 1/00006; A61B 1/00016; A61B 2560/0214
See application file for complete search history.

(56) References Cited

U.S. PATENT DOCUMENTS 4,895,164 A  *  1/1990  Wood ...................... A61B 5/01
                                                            374/124
5,743,644 A  *  4/1998  Kobayashi ............ G01J 5/0003
                                                            374/126

(Continued)

FOREIGN PATENT DOCUMENTS

| CN | 102026574 | 4/2011 |
| EP | 0747682 | 12/1996 |
| WO | 0016051 | 3/2000 |

OTHER PUBLICATIONS

"Office Action of Taiwan Counterpart Application", dated Jul. 27, 2016, p. 1-p. 20.
(Continued)

*Primary Examiner* — Natalie Huls
*Assistant Examiner* — Janice M Soto
(74) *Attorney, Agent, or Firm* — JCIPRNET (57) ABSTRACT

A hybrid detection apparatus including a detection device and a functional circuit is provided. The detection device is configured to execute a first detection function, so as to obtain first detection information. The functional circuit is suitable to be removably connected to the detection device. When the functional circuit is connected to the detection device, the detection device controls the functional circuit for performing a second detection function, so as to obtain second detection information. One of the first and the second detection functions is an image capturing function, and another one of the first and the second detection functions is a temperature detection function.

3 Claims, 5 Drawing Sheets

(51) Int. Cl.
  *A61B 1/05*   (2006.01)
  *A61B 1/055*  (2006.01)
  *A61B 1/07*   (2006.01)
  *A61B 1/247*  (2006.01)
  *A61B 5/00*   (2006.01)
  *A61B 5/01*   (2006.01)
  *A61B 1/24*   (2006.01)
  *G01J 5/00*   (2006.01)
  *A61B 1/233*  (2006.01)

(52) U.S. Cl.
  CPC ............... *A61B 1/05* (2013.01); *A61B 1/055* (2013.01); *A61B 1/07* (2013.01); *A61B 1/24* (2013.01); *A61B 1/247* (2013.01); *A61B 5/0077* (2013.01); *A61B 5/01* (2013.01); *A61B 5/6817* (2013.01); *G01J 5/0011* (2013.01); *A61B 1/233* (2013.01); *A61B 2560/0214* (2013.01); *G01J 2005/0077* (2013.01)

(56) References Cited

U.S. PATENT DOCUMENTS

| | | | |
|---|---|---|---|
| 5,790,586 A * | 8/1998 | Hilton, Jr. | G01J 5/02 374/124 |
| 7,787,938 B2 * | 8/2010 | Pompei | A61B 5/015 374/100 |
| 2011/0112791 A1 * | 5/2011 | Pak | A61B 1/227 702/131 |
| 2011/0228811 A1 * | 9/2011 | Fraden | G01J 5/061 374/130 |
| 2014/0275817 A1 | 9/2014 | Script | |

OTHER PUBLICATIONS

"Office Action of China Counterpart Application", dated Apr. 2, 2019, p1-p12, in which the listed references were cited.

* cited by examiner

HYBRID DETECTION APPARATUS

BACKGROUND OF THE INVENTION

1. Field of the Invention

The invention relates to a detection apparatus, and particularly relates to a hybrid detection apparatus capable of capturing an image and detecting a temperature.

2. Description of Related Art

The variation of human body temperature may be sign of many diseases. Thus, measuring and keeping track of body temperature is important in evaluating a patient's status. In the past, the body temperature is measured by inserting a mercury thermometer into the patient's mouth or armpit. However, such measurement takes a longer time and it is usually difficult to obtain the accurate body temperature. Thus, the infrared electronic thermometer (e.g., ear thermometer) becomes more and more popular in recent years. The ear thermometer is used by inserting the protruding probe part into the canal ear and sensing the infrared rays from the hypothalamus as the basis for measuring the body temperature. The ear thermometer is able to rapidly and accurately measure the body temperature.

Also, with the development of medical sciences and the electronic information technologies, the development of various endoscopes, such as otoscope, rhinoscope, and laryngoscope, that are inserted into the human body to detect diseases has also become more and more matured. Taking the otoscope as an example, since otitis media is a common disease for children, the otoscope is becoming a consumers' medical device for household use that conveniently allows parents to inspect their children at anytime and anywhere for a better household healthcare.

Sometimes an inflammatory ear cavity or throat may come with fever. Thus, in order to more carefully inspect the patient's symptoms, an ear thermometer and an endoscope are respectively required to obtain the patient's physiological information. However, in the normal household environment, it is seldom to have the ear thermometer and the endoscope at the same time. Even if the ear thermometer and the endoscope are available at the same time, how to use and store the ear thermometer and the endoscope is also a concern.

SUMMARY OF THE INVENTION

The invention provides a hybrid detection apparatus capable of solving the issues at hands.

A hybrid detection apparatus according to an embodiment of the invention includes an image capturing circuit, a temperature detecting circuit, a processing circuit, and a power circuit. The image capturing circuit is adapted to be controlled to perform an image capturing function and generate an image signal accordingly. The temperature detecting circuit is adapted to be controlled to perform a temperature detecting function and generate a temperature signal accordingly. The processing circuit is coupled to the image capturing circuit and the temperature detecting circuit and adapted to control operations of the image capturing circuit and the temperature detecting circuit, so as to output a detection image based on the image signal and output a detection temperature based on the temperature signal. The power circuit is coupled to the image capturing circuit, the temperature detecting circuit, and the processing circuit, so as to provide a working power required for operations of the circuits.

A hybrid detection apparatus according to an embodiment of the invention includes a detection apparatus and a functional circuit. The detection apparatus is adapted to perform a first detection function to obtain first detection information. The functional circuit is adapted to be removably installed on the detection apparatus. When the functional circuit is installed on the detection apparatus, the detection apparatus controls the functional circuit to perform a second detection function to obtain second detection information. One of the first detection function and the second detection function is an image capturing function and the other is a temperature detecting function.

A hybrid detection apparatus according to an embodiment of the invention includes a device body, an image capturing circuit, and a temperature detecting circuit. The image capturing circuit is adapted to be removably installed on the device body. When the image capturing circuit is installed on the device body, the image capturing circuit is controlled to perform an image capturing function and generate an image signal accordingly. The temperature detecting circuit is adapted to be removably installed on the device body. When the temperature detecting circuit is installed on the device body, the temperature detecting circuit is controlled to perform a temperature detecting function and generate a temperature signal accordingly. The device body outputs a detection image based on the image signal and outputs a detection temperature based on the temperature signal.

A functional circuit of a detection apparatus according to an embodiment of the invention includes an embedded part and a sensing part. The detection apparatus is adapted to perform a first detection function to obtain first detection information. The embedded part has a connection mechanism that is removably coupled to the detection apparatus. The sensing part is coupled to the embedded part and controlled to perform a second detecting function and generate a detection signal indicating second detection information accordingly. One of the first detection function and the second detection function is an image capturing function and the other is a temperature detecting function.

Based on above, the invention provides the hybrid detection apparatus integrating the temperature detecting function and the image capturing function. The user is able to conveniently expand the detection function of the already existing detection apparatus by using the single detection apparatus or disposing the additional functional circuit on the detection apparatus. Thus, the user does not need to separately use an endoscope and an ear thermometer to capture an image inside the body and detect the body temperature. Therefore, the invention creates a convenience when the user captures an image inside the body or detects the body temperature.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

In order to make the disclosure more comprehensible, embodiments are described below as the examples to show the disclosure. In the following embodiments, wordings used to indicate directions, such as "up," "down," "front," "back," "left," and "right", merely refer to directions in the accompanying drawings. Therefore, the directional wording is used to illustrate rather than limit the invention. Moreover, where possible, elements/components/steps with same reference numerals represent same or similar parts in the drawings and embodiments.

The disclosure provides a hybrid detection apparatus integrating a temperature detecting function and an image capturing function. The apparatus may be provided for a medical use or for detecting a physiological status by detecting the user's body temperature (e.g., ear temperature) and capturing a body image (e.g., an image inside the ear) of the user.

Based on the concept of the hybrid detection apparatus of the disclosure, four embodiments are described in the following to set forth various plausible hardware configurations of the hybrid detection apparatus. The hardware configurations may be generally divided into a configuration of integral formation and a configuration of removable circuits.

In addition, the configuration of integral formation is carried out by integrating the temperature detecting function and the image capturing function in a single apparatus. Such configuration will be described in the first embodiment. The configuration of removable circuits is carried out by implementing at least one of the temperature detecting function and the image capturing function in a removable circuit, so as to additionally provide an image capturing/temperature detecting function to an independent apparatus by disposing a plug-in functional circuit in the independent apparatus. Such type of arrangement is described in the following with reference to the second to fourth embodiments.

Figure 1A:
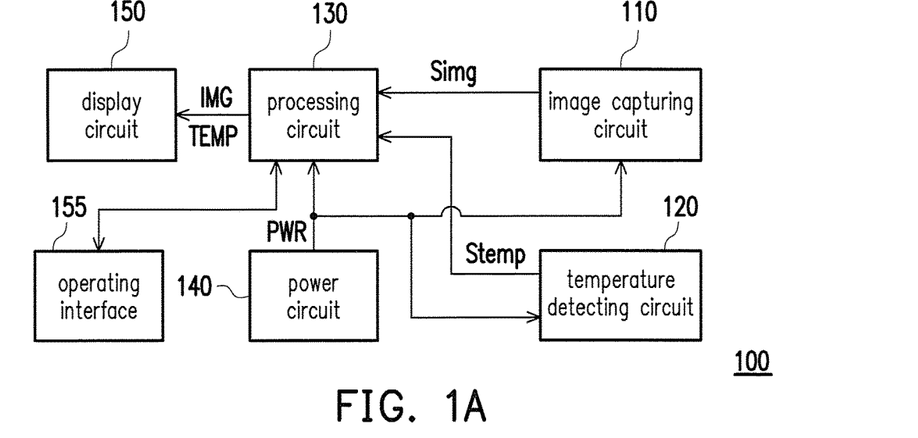
FIG. 1A is a schematic functional block view illustrating a hybrid detection apparatus according to a first embodiment of the invention.
Figure 1B:
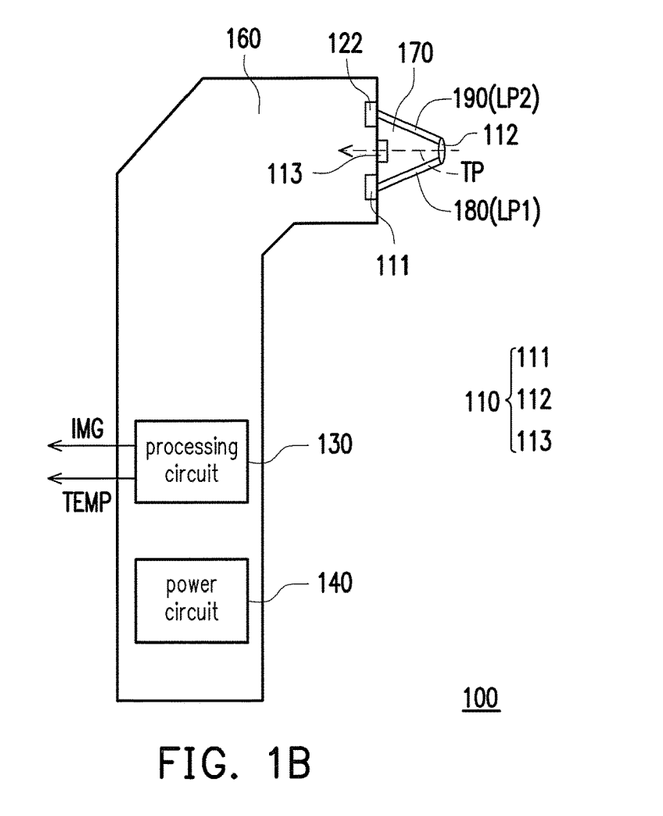
FIG. 1B is a schematic view illustrating a hardware arrangement of the hybrid detection apparatus according to the first embodiment of the invention.

FIG. 1A is a schematic functional block view illustrating a hybrid detection apparatus according to a first embodiment of the invention. FIG. 1B is a schematic view illustrating a hardware arrangement of the hybrid detection apparatus according to the first embodiment of the invention. In the following, functions of the respective circuits of a hybrid detection apparatus 100 are firstly described in the following with reference to FIG. 1A. Then, all the components of the hybrid detection apparatus 100 and an arrangement of the components are described with reference of FIG. 1B. The subsequent embodiments are also described in a similar way.

Referring to FIG. 1A, in this embodiment, the hybrid detection apparatus 100 includes an image capturing circuit 110, a temperature detecting circuit 120, a processing circuit 130, a power circuit 140, a display circuit 150, and an operating interface 160.

The image capturing circuit 110 may be controlled to perform an image capturing function and generate an image signal Simg accordingly. The temperature detecting circuit 120 may be controlled to perform a temperature detecting function and generate a temperature signal Stemp accordingly.

The processing circuit 130 is coupled to the image capturing circuit 110, the temperature detecting circuit 120, the power circuit 140, the display circuit 150, and the operating interface 155 to control operations of the circuits, receive the image signal Simg generated by the image capturing circuit 110 and the temperature signal Stemp generated by the temperature detecting circuit 120, and perforin signal processing. The processing circuit 130 may perform image signal processing (e.g., sampling, noise filtering, gray-scale converting, etc., but the invention is not limited thereto) on the image signal Simg to output a detection image IMG and perform temperature signal processing (e.g., signal leveling, filtering, amplifying, etc., but the invention is not limited thereto) to output a detection temperature TEMP. Here, the processing unit 130 may include a central processing unit (CPU) or other general/specific-purpose programmable microprocessor, a digital signal processor (DSP), a programmable controller, an application specific integrated circuit (ASIC), a programmable logic device (PLD), or other similar apparatus or a combination thereof.

The power circuit 140 is coupled to the image capturing circuit 110, the temperature detecting circuit 120, the processing circuit 130, and the display circuit 150. The power circuit 140 may provide a working power PWR required for the operations of the circuits.

The display circuit 150 is coupled to the processing circuit 130 and the power circuit 140 and is adapted to display information such as the detection image IMG and the detection temperature TEMP for the user's viewing.

It should be noted that the display circuit 150 of this embodiment may be optionally disposed in the hybrid detection apparatus 100. In other embodiments, the hybrid detection apparatus 100 may include only the image capturing circuit 110, the temperature detecting circuit 120, the processing circuit 130, and the power circuit 140.

In addition, in a configuration where the hybrid detection apparatus 100 does not include the display circuit 150, the processing circuit 130 may, for example, output information associated with the detection image IMG and the detection temperature TEMP to an external electronic apparatus through wired/wireless transmission, so as to use the external electronic apparatus to display the detection image IMG and the detection temperature TEMP. However, the invention is not limited thereto.

Referring to FIGS. 1A and 1B together, from a perspective incorporating the hardware arrangement, the hybrid detection apparatus 100 further includes a holding part 160, a probe part 170, and light guide units 180 and 190 in addition to the circuits 110 to 150.

The holding part 160 and the probe part 170 are cases with accommodating spaces therein, for example. The holding part 160 may serve as a handle of the hybrid detection apparatus 100 for the user to operate and hold the hybrid detection apparatus 100. The processing circuit 130 and the power circuit 140 may be disposed in the accommodating space of the holding part 160, and are connected to the image capturing circuit 110 and the temperature detecting circuit 120 through wires.

The probe part 170 is in a cone shape. One end of the probe part 170 having a smaller radius is defined as the front end, whereas the other end of the probe part 170 having a greater radius is defined as the rear end. The read end of the probe part 170 is connected to the holding part 160. The front end of the probe part 170 is suitable to be inserted into the inside of the human body, such as being inserted into the ear cavity, the oral cavity, the nasal cavity, etc., such that the image capturing circuit 110 may capture an image inside the human body, or the temperature detecting circuit 120 may sense infrared rays irradiated from the human body.

The light guide units 180 and 190 are disposed in the probe part 170. The light guide unit 180 serves to provide a light transmission path LP1 between the front end and the rear end of the probe part 170 to the image capturing circuit 110, and the light guide unit 190 serves to provide another light transmission path LP2 to the temperature detecting circuit 120. The light transmission path LP1 and the light transmission path LP2 substantially do not interfere with each other. In this embodiment, the light guide units 180 and 190 may be implemented as an optical fiber bundle or a light guide structure. However, the invention is not limited thereto. Moreover, the light guide units 180 and 190 may be arranged inside the probe part 170 to surround and be attached to an inner surface of the probe part 170. However, the invention is not limited thereto.

Specifically, the image capturing circuit 110 of this embodiment includes a light source 111, a lens set 112, and an image sensor 113. In addition, the temperature detecting circuit 120 includes an infrared sensor 122.

In the image capturing circuit 110 of this embodiment, the light source 111 may be disposed in the holding part 160 or the probe part 170. However, the invention is not limited thereto. One end of the light guide unit 180 is disposed in correspondence with a position of the light source 111. In addition, the other end of the light guide unit 180 extends to the front end of the probe part 170. Thus, a light beam of the light source 111 may be emitted out of the front end of the probe part 170 through the light transmission path LP1 provided by the light guide unit 180. Here, the light source 111 may be implemented as a light emitting diode, for example. However, the invention is not limited thereto.

The lens set 112 is disposed at the front end of the probe part 170 and is adapted to collect light beams and provide the light beams to the image sensor 113 disposed on a light transmission path TP of the lens set 112. Thus, the image sensor 113 may sense a light intensity and convert the light intensity into the image signal Simg in a form of electrical signal. The image sensor 113 of this embodiment may include a light sensor, for example. The light sensor may be a charge coupled device (CCD), a complementary metal-oxide semiconductor (CMOS), or other similar components, for example. However, the invention is not limited thereto.

It should be noted that, if the image capturing circuit 110 of this embodiment is used to capture an image in the canal ear, the lens set 112 and the image sensor 113 may be designed to focus at a position 10 mm to 20 mm in the front, such that the detection image IMG may clearly show an image of the eardrum. If the image capturing circuit 110 of this embodiment is used to capture an image in the oral cavity, the lens set 112 and the image sensor 113 may be designed to focus at a position 10 mm to 160 mm in the front, such that the detection image IMG may clearly show parts such as uvula, tonsil, velum, and throat wall, etc., in the oral cavity. However, the invention is not limited thereto.

In the temperature detecting circuit 120 of this embodiment, the infrared sensor 122 may be disposed in the holding part 160 and the probe part 170. However, the invention is not limited thereto. One end of the light guide unit 190 is disposed in correspondence with a position of the infrared sensor 122. In addition, the other end of the light guide unit 190 extends to the front end of the probe part 170. Thus, infrared rays at an outer side of the probe part 170 may be received by the infrared sensor 122 through the light transmission path LP2 provided by the light guide unit 190, and the infrared sensor 122 may generate the temperature signal Stemp associated with a temperature value based on a frequency or wavelength of the received infrared rays accordingly.

It should also be noted that, in an exemplary embodiment, an outer part of the infrared sensor 122 may be coated with a heat insulating material (e.g., an alloy material having a greater thermal capacity such as a zinc alloy or similar materials), so as to prevent the sensing of the infrared sensor 122 from becoming less accurate due to a temperature change of a component nearby or a temperature change in the surrounding.

With said arrangement, the hybrid detection apparatus 100 of this embodiment may serve as an endoscope (e.g., otoscope, rhinoscope, and laryngoscope, etc.) for detecting the inside of the human body or serve as an ear thermometer or a forehead thermometer that detects the body temperature.

More specifically, when the hybrid detection apparatus 100 serves as an endoscope and captures/shoots an image inside the ear, for example, the user may operate the operating interface 155 (configured as pressing buttons, for example, but the invention is not limited thereto) of the hybrid detection apparatus 100 to provide a control command, so as to enable the image capturing circuit 110 and disable the temperature detecting circuit 120.

When the image capturing circuit 110 is enabled, the light source 111 is lightened up, such that a light beam emitted by the light source 111 is transmitted to the outer side of the probe part 170 through the light transmission path LP1, thereby illuminating the inside of the ear. The lens set 112 may collect the light beam in the inside of the ear and provide the collected light beam to the image sensor 113, such that the image sensor 113 generates the corresponding image signal Simg. The image signal Simg is transmitted to the processing circuit 130 for image processing, and the detection image IMG of the inside of the ear is output.

Alternatively, when the hybrid detection apparatus 110 serves as an ear thermometer, the user may also operate the operating interface of the hybrid detection apparatus 100 to provide a control command, so as to disable the image capturing circuit 110 and enable the temperature detecting circuit 120.

When the temperature detecting circuit 120 is enabled, the infrared sensor 122 may receive infrared rays irradiated from hypothalamus from the front end of the probe part 170 through the light transmission path LP2. The infrared sensor 122 may detect the wavelength or frequency of the received infrared rays and generate the corresponding temperature signal Stemp accordingly. The temperature signal Stemp is transmitted to the processing circuit 130 for signal processing, and outputs the detection temperature TEMP indicating the ear temperature.

Based on above, the image capturing function and the temperature detecting function of this embodiment are integrated into the single hybrid detection apparatus 100. Thus, the user does not need to separately use an endoscope and an ear thermometer to capture an image inside the body and detect the body temperature. Thus, the hybrid detection apparatus 100 creates convenience for the user.

Also, since the infrared sensor 122 receives the external infrared rays through the light guide unit 190, a position where the infrared sensor 122 is disposed in the detection apparatus 100 may be adjusted based on needs. In other words, the infrared sensor 122 of this embodiment does not need to be disposed near the image sensor 113. By adjusting a position where the light guide unit 190 is disposed and a length of the light guide unit 190, the infrared sensor 122 may be disposed at a position in a predetermined distance from the image sensor 113, so as to prevent heat generated when the image sensor 113 is operating from affecting the temperature sensing of the infrared sensor 122.

Figure 2A:
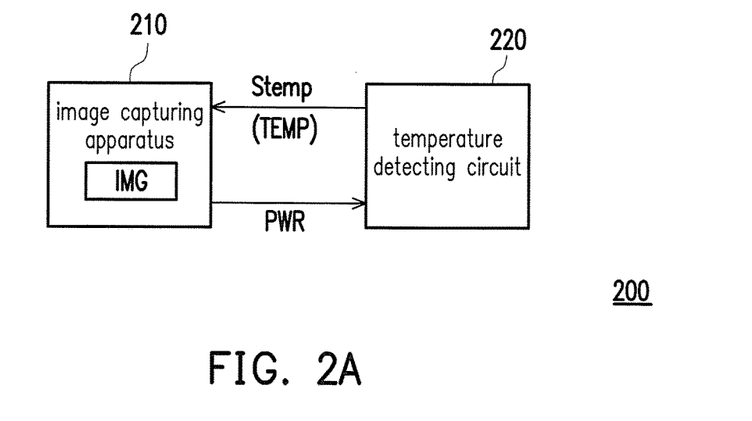
FIG. 2A is a schematic functional block view illustrating a hybrid detection apparatus according to a second embodiment of the invention.
Figure 2B:
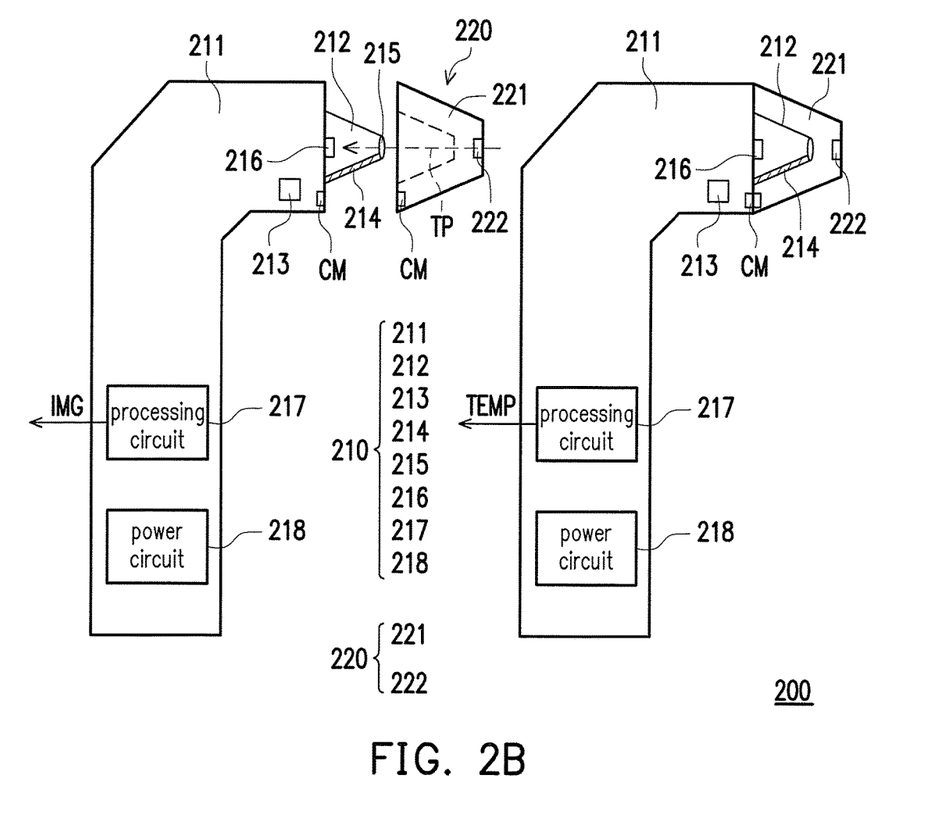
FIG. 2B is a schematic view illustrating a hardware arrangement of the hybrid detection apparatus according to the second embodiment of the invention.

FIG. 2A is a schematic functional block view illustrating a hybrid detection apparatus according to a second embodiment of the invention. FIG. 2B is a schematic view illustrating a hardware arrangement of the hybrid detection apparatus according to the second embodiment of the invention.

Referring to FIG. 2A, in this embodiment, a hybrid detection apparatus 200 includes an image capturing apparatus 210 and a temperature detecting circuit 220.

The image capturing apparatus 210 is an independently operating apparatus, and may be an endoscope such as otoscope, rhinoscope, and laryngoscope, etc. The image capturing apparatus 210 may serve to perform an image capturing function to obtain the detection image IMG. The temperature detecting circuit 220 is an expanded circuit of the image capturing apparatus 210 and is unable to operate independently. The temperature detecting circuit 220 is suitable to be removably installed on the image capturing apparatus 210. When the temperature detecting circuit 220 is installed on the image capturing apparatus 210, the image capturing apparatus 210 may provide the temperature detecting circuit 220 with the working power PWR and control the temperature detecting circuit 220 to perform the temperature detecting function, such that the temperature detecting circuit 220 may transmit the temperature signal Stemp to the image capturing apparatus 210. The image capturing apparatus 210 may perform signal processing on the temperature signal Stemp, so as to obtain the corresponding detection temperature TEMP.

In addition, similar to the first embodiment, the image capturing apparatus 210 of this embodiment may further include a display circuit (not shown) to display the obtained information such as the detection image IMG and the detection temperature TEMP for the user's viewing.

Referring to FIGS. 2A and 2B, from a perspective incorporating the hardware arrangement, the image capturing apparatus 210 of this embodiment includes a holding part 211, a probe part 212, a light source 213, a light guide unit 214, a lens set 215, an image sensor 216, a processing circuit 217, and a power circuit 218, and the temperature detecting circuit 220 includes an embedded part 221 and an infrared sensor 222.

In the image capturing apparatus 210 of this embodiment, an arrangement of the holding part 211 and the probe part 212 is similar to the arrangement of the holding part 160 and the probe part 170 of the first embodiment. Thus, details in this respect will not be repeated in the following. The holding part 211 of this embodiment differs from the first embodiment in that the holding part 211 has a connection mechanism CM corresponding to the temperature detecting circuit 220. Thus, the temperature detecting circuit 220 may be engaged with the image capturing apparatus 210 by using the connection mechanism CM (e.g., fixed by rotating joining), and be electrically connected to the image capturing apparatus 210 through wires inside the connection mechanism CM.

The light source 213 may be disposed in the holding part 211 or the probe part 212. However, the invention is not limited thereto. The light guide unit 214 is disposed in the probe part 212. Here, one end of the light guide unit 214 is disposed in correspondence with a position of the light source 213. In addition, the other end of the light guide unit 214 extends to the front end of the probe part 212. Thus, a light beam of the light source 213 may be emitted out of the front end of the probe part 212 through the light transmission path LP provided by the light guide unit 214. Here, the light source 213 may be implemented as a light emitting diode, for example, and the light guide unit 214 may be implemented as an optical fiber bundle, for example. However, the invention is not limited thereto.

The lens set 215 is disposed at the front end of the probe part 212 and is adapted to collect light beams and provide the light beams to the image sensor 216 disposed on the light transmission path TP of the lens set 112. Thus, the image sensor 216 may sense a light intensity and convert the light intensity into the image signal Simg in a form of electrical signal.

The processing circuit 217 and the power circuit 218 are disposed in the holding part 211. The processing circuit 217 may control operations of the light source 213 and the image sensor 216 when the image capturing apparatus 210 is used separately, and perform image signal processing on the image signal Simg generated by the image sensor 216 to output the detection image IMG. In addition, the processing circuit 217 may control an operation of the infrared sensor 222 when the temperature detecting circuit 220 is installed on the image capturing apparatus 210, and perform temperature signal processing on the temperature signal Stemp generated by the infrared sensor 222 to output the detection temperature TEMP. The power circuit 218 is adapted to provide the working power PWR required for the operations of the light source 213, the image sensor 216, the processing circuit 217, and the infrared sensor 222.

In the temperature detecting circuit 220 of this embodiment, the embedded part 221 has an accommodating space corresponding to a shape of the probe part 212 and the connection mechanism CM. As shown in FIG. 2B, if the probe part 212 is in a cone shape, the embedded part 221 also has a corresponding cone-shaped accommodating space. Thus, when the image capturing apparatus 210 and the temperature detecting circuit 220 are engaged through the connection mechanism CM, the probe part 212 may be accommodated in the accommodating space of the embedded part 221.

The infrared sensor 222 is disposed at a top end of the embedded part 221 and faces an outer side to receive infrared rays. Based on a frequency or a wavelength of the received infrared rays, the infrared sensor 222 generates the temperature signal Stemp associated with a temperature value.

With such arrangement, the image capturing apparatus 210 of this embodiment may independently serve as an endoscope for detecting the inside of the human body, and may serve as an ear thermometer or a forehead thermometer for detecting the body temperature when the temperature detecting circuit 220 is installed on the image capturing apparatus 210.

More specifically, when the user intends to use the image capturing function of the hybrid detection apparatus 200, the user only needs to use the image capturing apparatus 210 to shoot/capture an image inside the human body. An image capturing operation of the image capturing apparatus 210 is similar to the first embodiment. Thus, details in this respect will not be repeated in the following.

When the user intends to use the temperature detecting function of the hybrid detection apparatus 200, the user needs to install the temperature detecting circuit 220 on the image capturing apparatus 210. When the processing circuit 217 determines that the temperature detecting circuit 220 is electrically connected to the image capturing apparatus 210, the processing circuit 217 may enable the infrared sensor 222, and the power circuit 218 may provide the working power PWR to the infrared sensor 222. A temperature detecting operation of the infrared sensor 222 is similar to the first embodiment. Thus, details in this respect will not be repeated in the following. Also, when the processing circuit 217 determines that the temperature detecting circuit 220 is electrically connected to the image capturing apparatus 210, the processing circuit 217 may disable the image capturing function of the image capturing apparatus 210 and instruct the power circuit 218 to stop providing the working power PWR to the circuits performing the image capturing function.

Based on the above, in this embodiment, the removable temperature detecting circuit 220 is provided on the hardware basis of the image capturing apparatus 210, so as to offer an expanded temperature detecting function. Thus, the user only needs to install the additional temperature detecting circuit 220 to carry out the temperature detecting function by using the image capturing apparatus 210. Thus, the apparatus also creates convenience for the user.

Figure 3A:
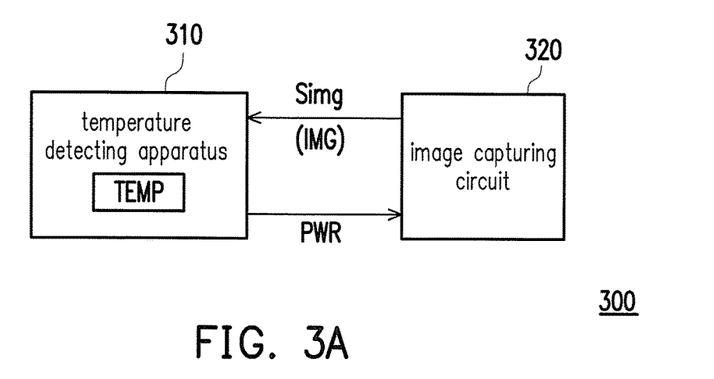
FIG. 3A is a schematic functional block view illustrating a hybrid detection apparatus according to a third embodiment of the invention.
Figure 3B:
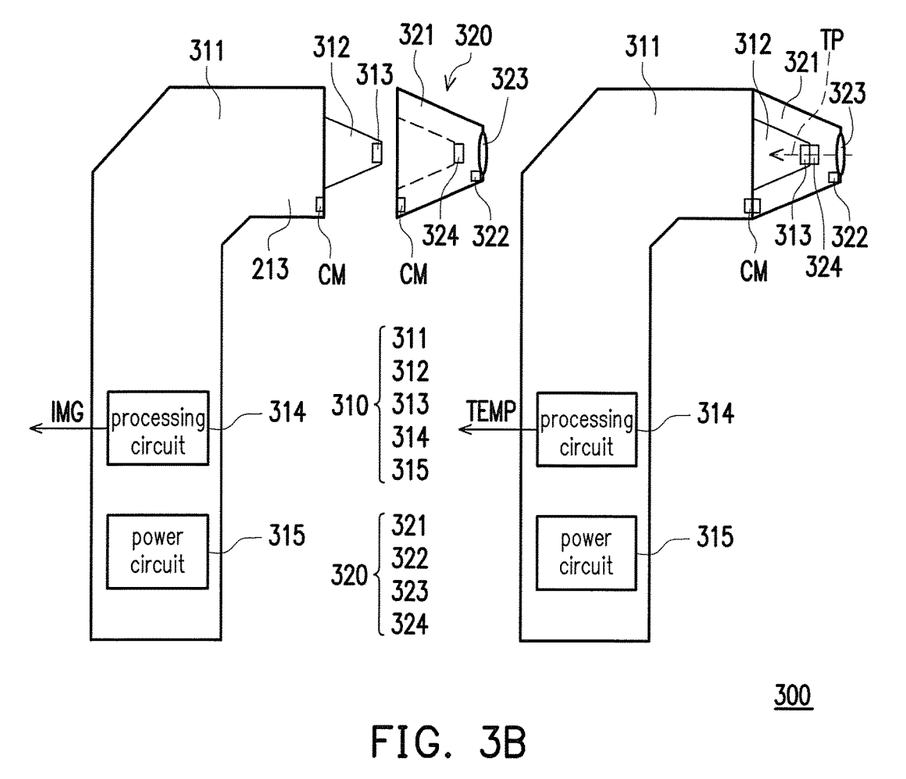
FIG. 3B is a schematic view illustrating a hardware arrangement of the hybrid detection apparatus according to the third embodiment of the invention.

FIG. 3A is a schematic functional block view illustrating a hybrid detection apparatus according to a third embodiment of the invention. FIG. 3B is a schematic view illustrating a hardware arrangement of the hybrid detection apparatus according to the third embodiment of the invention.

Referring to FIG. 3A, in this embodiment, a hybrid detection apparatus 300 includes a temperature detecting apparatus 310 and an image capturing circuit 320.

The temperature detecting apparatus 310 is an independently operating apparatus, and may be an apparatus such as an ear thermometer or a forehead thermometer, etc. The temperature detecting apparatus 310 may serve to perform a temperature detecting function to obtain the detection temperature TEMP. The image capturing circuit 320 is an expanded circuit of the temperature detecting apparatus 310 and is unable to operate independently. The image capturing circuit 320 is suitable to be removably installed on the temperature detecting apparatus 310.

When the image capturing circuit 320 is installed on the temperature detecting apparatus 310, the temperature detecting apparatus 310 may provide the working power PWR to the image capturing circuit 320 and control the image capturing circuit 320 to perform the image capturing function, such that the image capturing circuit 320 may transmit the image signal Simg to the temperature detecting apparatus 310. The temperature detecting apparatus 310 may perform signal processing on the image signal Simg, so as to obtain the corresponding detection image IMG.

In addition, similar to the first embodiment, the temperature detecting apparatus 310 of this embodiment may further include a display circuit (not shown) to display the obtained information such as the detection image IMG and the detection temperature TEMP for the user's viewing.

Referring to FIGS. 3A and 3B, from a perspective incorporating the hardware arrangement, the temperature detecting apparatus 310 of this embodiment includes a holding part 311, a probe part 312, an infrared sensor 313, a processing circuit 314, and a power circuit 315, and the image capturing circuit 320 includes an embedded part 321, a light source 322, a lens set 323, and an image sensor 324.

In the temperature detecting apparatus 310 of this embodiment, an arrangement of the holding part 311 and the probe part 312 is similar to the arrangement of the holding part 211 and the probe part 212 of the second embodiment. Thus, details in this respect will not be repeated in the following. The image capturing circuit 320 may be engaged with the temperature detecting apparatus 310 through the connection mechanism CM and electrically connected to the temperature detecting apparatus 310 through wires inside the connection mechanism CM.

In the temperature detecting apparatus 310 of this embodiment, the infrared sensor 313 is disposed at a top end of the probe part 312 and faces an outer side to receive infrared rays. Based on a frequency or a wavelength of the received infrared rays, the infrared sensor 313 generates the temperature signal Stemp associated with a temperature value.

The processing circuit 314 and the power circuit 315 are disposed in the holding part 311. The processing circuit 314 may control an operation of the infrared sensor 313 when the temperature detecting apparatus 310 is used separately, and perform signal processing on the temperature signal Stemp generated by the infrared sensor 313 to output the detection temperature TEMP. Also, the processing circuit 314 may control operations of the light source 322 and the image sensor 324 when the image capturing circuit 320 is installed on the temperature detecting apparatus 310, and perform image signal processing on the image signal Simg generated by the image sensor 324 to output the detection image IMG. The power circuit 315 is adapted to provide the working power PWR required for the operations of the infrared sensor 313, the processing circuit 314, the light source 322, and the image sensor 324. Also, when the processing circuit 314 determines that the image capturing circuit 320 is electrically connected to the temperature detecting apparatus 310, the processing circuit 314 may disable the temperature detecting function of the temperature detecting apparatus 310 and instruct the power circuit 315 to stop providing the working power PWR to the circuits performing the temperature detecting function.

In the image capturing circuit 320 of this embodiment, the embedded part 321 has an accommodating space corresponding to a shape of the probe part 312 and the connection mechanism CM. As shown in FIG. 3B, if the probe part 312 is in a cone shape, the embedded part 321 also has a corresponding cone-shaped accommodating space. Thus, when the temperature detecting apparatus 310 and the image capturing circuit 320 are engaged through the connection mechanism CM, the probe part 312 may be accommodated in the accommodating space of the embedded part 321.

The light source 322 may be disposed on the embedded part 321 and face the outer side. The lens set 323 is disposed at the front end of the embedded part 321 and is adapted to collect light beams and provide the light beams to the image sensor 324 disposed on the light transmission path TP of the lens set 323. Thus, the image sensor 324 may sense a light intensity and convert the light intensity into the image signal Simg in a form of electrical signal.

With such arrangement, the temperature detecting apparatus 310 of this embodiment may independently serve as an ear thermometer or a forehead thermometer for detecting the body temperature, and may serve as an endoscope for detecting the inside of the human body when the image capturing circuit 320 is disposed on the temperature detecting apparatus 310.

More specifically, when the user intends to use the temperature detecting function of the hybrid detection apparatus 300, the user may use only the temperature detecting apparatus 310 to detect the body temperature. A temperature detecting operation of the temperature detecting apparatus 310 is similar to the first embodiment. Thus, details in this respect will not be repeated in the following.

When the user intends to use the image capturing function of the hybrid detection apparatus 300, the user needs to install the image capturing circuit 320 on the temperature detecting apparatus 310. When the processing circuit 314 determines that the image capturing circuit 320 is electrically connected to the temperature detecting apparatus 310, the processing circuit 314 may enable the light source 322 and the image sensor 324 and the power circuit 315 may provide the working power PWR to the light source 322 and the image sensor 324. An image capturing operation of the image capturing circuit 320 is similar to the first embodiment. Thus, details in this respect will not be repeated in the following.

Based on the above, in this embodiment, the removable image capturing circuit 320 is provided on the hardware basis of the temperature detecting apparatus 310, so as to offer an expanded image capturing function. Thus, the user only needs to install the additional image capturing circuit 320 to capture an image by using the temperature detecting apparatus 310. Thus, the apparatus also creates convenience for the user.

More specifically, in the second and third embodiments, the detection apparatus is used with the removable functional circuit to simultaneously perform image capturing and temperature detection. Namely, the detection apparatus itself has a specific detection function, and the user may additionally dispose the functional circuit on the detection apparatus, so that the detection apparatus has an additional detection function.

In other words, the disclosure provides a removable functional circuit (e.g., the temperature detection circuit 220 and the image capturing circuit 320). The removable functional circuit may be used in the detection apparatus already having a detection function, so as to provide an expanded detection function. Also, the removable functional circuit may be used in any electronic apparatus compatible with a hardware arrangement of the functional circuit, so as to provide the expanded detection function. As shown in the second and third embodiments, the functional circuit provided in the disclosure at least includes an embedded part (e.g., the embedded part 221, 321) and a sensing part (e.g., the infrared sensor 222 of the temperature detecting circuit 220 and the light source 322, the lens set 323, and the image sensor 324 of the image capturing circuit 320). The embedded part has a connection mechanism (e.g., the connection mechanism CM) removably coupled to the detection apparatus (e.g., the image capturing apparatus 210 and the temperature detecting apparatus 310). The sensing part is a hardware part adapted to be controlled to perform a specific detection function.

Figure 4A:
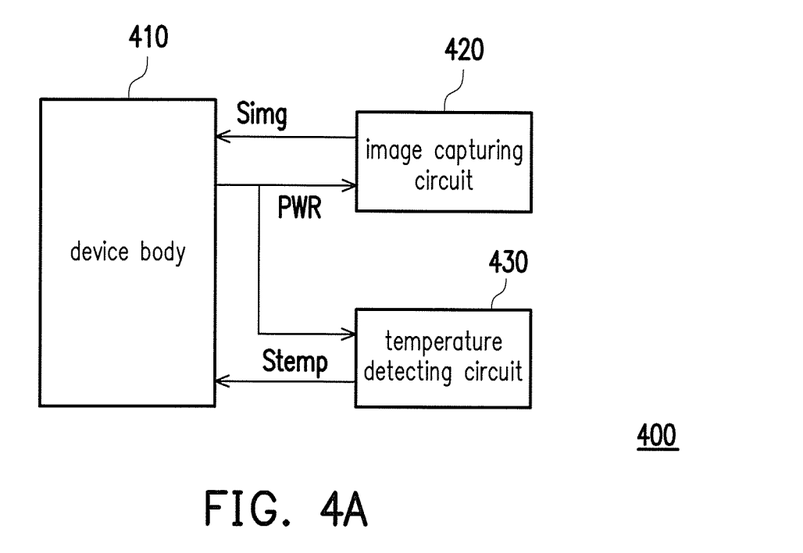
FIG. 4A is a schematic functional block view illustrating a hybrid detection apparatus according to a fourth embodiment of the invention.
Figure 4B:
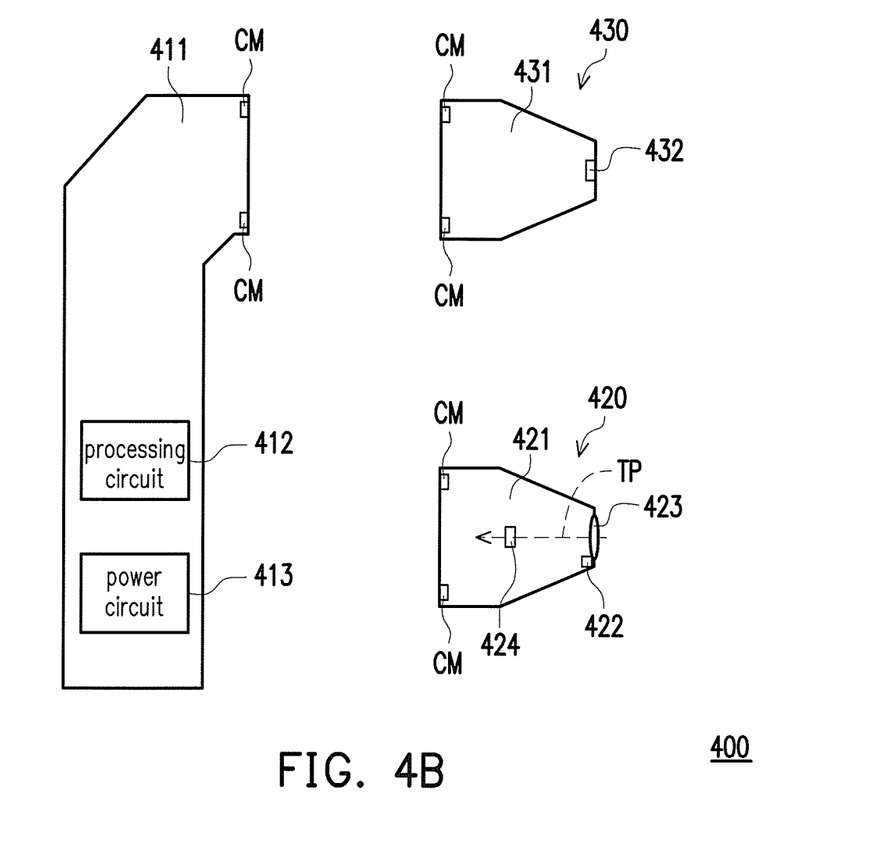
FIG. 4B is a schematic view illustrating a hardware arrangement of the hybrid detection apparatus according to the fourth embodiment of the invention.

FIG. 4A is a schematic functional block view illustrating a hybrid detection apparatus according to a fourth embodiment of the invention. FIG. 4B is a schematic view illustrating a hardware arrangement of the hybrid detection apparatus according to the fourth embodiment of the invention.

Referring to FIG. 4A, in this embodiment, a hybrid detection apparatus 400 includes a device body 410, an image capturing circuit 420, and a temperature detecting circuit 430.

The image capturing circuit 420 and the temperature detecting circuit 430 of this embodiment are designed as removable expanded circuits and need to be used with the device body 410 to operate. The device body 410 of this embodiment may be implemented as any electronic apparatus that operates independently, or may be implemented as a hardware arrangement that requires the image capturing circuit 420 and the temperature detecting circuit 430 to operate.

When the image capturing circuit 420 is disposed on the device body 410, the image capturing circuit 420 may be controlled to perform an image capturing function, generate the image signal Simg accordingly, and transmit the image signal Simg to the device body 410. The device body 410 may perform image signal processing based on the image signal Simg and output the detection image IMG accordingly.

When the image detecting circuit 430 is disposed on the device body 410, the temperature detecting circuit 430 is controlled to perform the temperature detecting function, generate the temperature signal Stemp, and transmit the temperature signal Stemp to the device body 410. The device body 410 may perform temperature signal processing based on the temperature signal Stemp, and output the detection temperature TEMP accordingly.

In addition, similar to the first embodiment, the device body 410 of this embodiment may further include a display circuit (not shown) to display the obtained information such as the detection image IMG and the detection temperature TEMP for the user's viewing.

Referring to FIGS. 4A and 4B, from a perspective incorporating the hardware arrangement, the device body 410 of this embodiment includes a holding part 411, a processing circuit 412, and a power circuit 413, the image capturing circuit 420 includes a probe part 421, a light source 422, a lens set 423, and an image sensor 424, and the temperature detecting circuit 430 includes a probe part 431 and an infrared sensor 432.

In the device body 410 of this embodiment, the holding part 411 has the connection mechanism CM and an accommodating space. The processing circuit 412 and the power circuit 413 are disposed in the accommodating space of the holding part 411. In addition, the processing circuit 412 and the power circuit 413 are used to control operations of the image capturing circuit 420 and the temperature detecting circuit 430 and provide the working power PWR when the image capturing circuit 420 and/or the temperature detecting circuit 430 are/is connected to the device body 410.

In the image capturing circuit 420 of this embodiment, the probe part 421 has the connection mechanism CM corresponding to the holding part 411 of the device body 410. The light source 422 is disposed on the probe part 421 and face an outer side. The lens set 423 is disposed at the front end of the probe part 421 and is adapted to collect light beams and provide the light beams to the image sensor 424 disposed on the light transmission path TP of the lens set 112. Thus, the image sensor 424 may sense a light intensity and convert the light intensity into the image signal Simg in a form of electrical signal.

In the temperature detecting circuit 430 of this embodiment, the infrared sensor 432 is disposed at a top end of the probe part 431 and faces the outer side to receive infrared rays. Based on a frequency or a wavelength of the received infrared rays, the infrared sensor 432 generates the temperature signal Stemp associated with a temperature value.

With such arrangement, the device body 410 of this embodiment may be used as an endoscope for detecting the inside of the human body when used with the image capturing circuit 420, and the device body 410 of this embodiment may be used as an ear thermometer or a forehead thermometer for detecting the body temperature when used with the temperature detecting circuit 430.

The embodiment differs from the second and third embodiments in that the device body itself does not have the image capturing or temperature detecting function, and the image capturing and temperature detecting functions are respectively carried out by external functional circuits. Thus, when the user intends to use the image capturing function of the hybrid detection apparatus 400, the user needs to install the image capturing circuit 420 on the device body 410. When the user intends to use the temperature detecting function of the hybrid detection apparatus 400, the user needs to install the temperature detecting circuit 430 on the device body 410.

Based on the above, in this embodiment, multiple functional circuits that have different detection functions and are removable are provided on the basis of any hardware having a processing function and a power supplying function, so as to provide expanded temperature detecting or image capturing function. Thus, the user only needs to install the additional image capturing circuit 420 or the additional temperature detecting circuit 430 to capture an image or detect a temperature by using the device body 410. Thus, the apparatus also creates convenience for the user.

In other words, in light of the concept of the disclosure, the hybrid detection apparatus may be implemented as an integrally formed hybrid detection apparatus (e.g., the first embodiment), an image capturing apparatus used with a removable ear temperature detecting circuit (e.g., the second embodiment), or a temperature detecting apparatus used with a removable image capturing circuit (e.g., the third embodiment), or implemented by using an electronic apparatus having a computing function and a power supplying function as the device body with a removable image capturing circuit and a removable temperature detecting circuit (e.g., the fourth embodiment).

Figure 5:
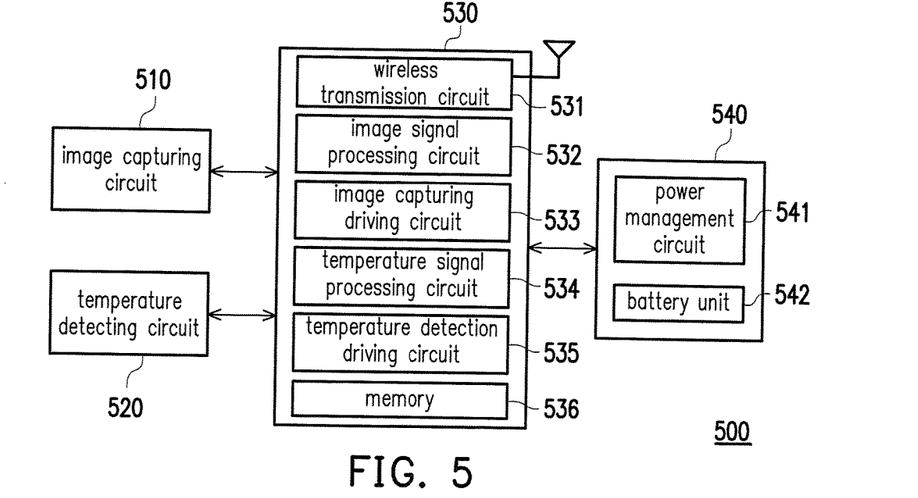
FIG. 5 is a functional block view illustrating circuits of a hybrid detection apparatus according to an embodiment of the invention.

In the following, circuit arrangements of the hybrid detection apparatus of the disclosure in different embodiments are described with reference to FIGS. 5 and 6. FIG. 5 is a functional block view illustrating circuits of a hybrid detection apparatus according to an embodiment of the invention.

Figure 6:
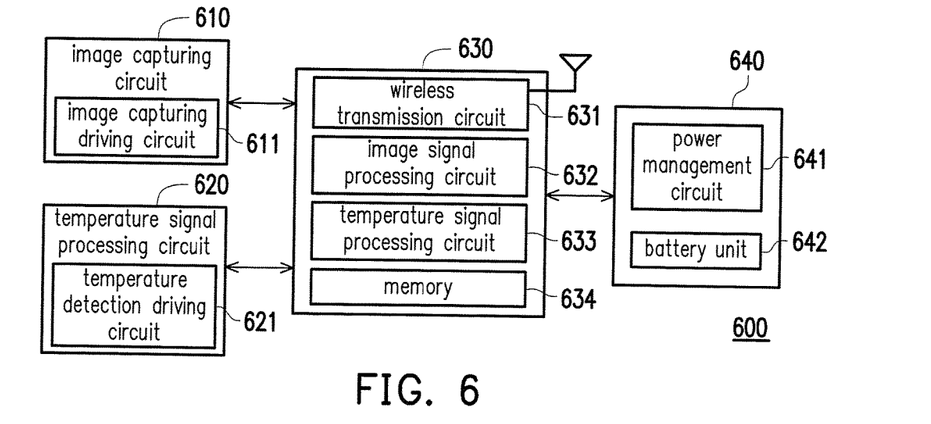
FIG. 6 is a functional block view illustrating circuits of a hybrid detection apparatus according to another embodiment of the invention.

FIG. 6 is a functional block view illustrating circuits of a hybrid detection apparatus according to another embodiment of the invention.

Referring to FIG. 5, a hybrid detection apparatus 500 includes an image capturing circuit 510, a temperature detecting circuit 520, a processing circuit 530, and a power circuit 540. In addition, the image capturing circuit 510 and the temperature capturing circuit 520 may be arranged in accordance with the first to fourth embodiments. The processing circuit 530 includes a wireless transmission circuit 531, an image signal processing circuit 532, an image capturing driving circuit 533, a temperature signal processing circuit 534, a temperature detection driving circuit 535, and a memory 536. The power circuit 540 includes a power management circuit 541 and a battery unit 542.

In the processing circuit 530, the image capturing driving circuit 533 and the temperature detection driving circuit 535 may be respectively adapted to drive the image capturing circuit 510 and the temperature detecting circuit 520 to make the image capturing circuit 510 and the temperature detecting circuit 520 respectively transmit the image signal Simg and the temperature signal Stemp. The image signal processing circuit 532 and the temperature signal processing circuit 534 may respectively receive the image signal Simg and the temperature signal Stemp. Also, necessary information is read from the memory 536 to respectively perform signal processing on the image signal Simg and the temperature signal Stemp, so as to generate the detection image IMG and the detection temperature TEMP.

The detection image IMG generated by the image signal processing circuit 532 and the detection temperature TEMP generated by the temperature signal processing circuit 534 may be transmitted to an external electronic apparatus through the wireless transmission circuit 531 to allow the user to view a detection result by using the external electronic apparatus.

It should be noted that, in practice, the functions of the image signal processing circuit 532 and the temperature signal processing circuit 534 may be integrated in one processing chip. However, the invention is not limited thereto.

In the power circuit 540, the power management circuit 541 is adapted to modulate charging and discharging of the battery unit 542, so as to control an intensity of the working power PWR provided to the respective circuits.

Referring to FIG. 6, a hybrid detection apparatus 600 includes an image capturing circuit 610, a temperature detecting circuit 620, a processing circuit 630, and a power circuit 640. The embodiment is similar to the embodiment shown in FIG. 5, except for a main difference that an image capturing driving circuit 611 and a temperature detection driving circuit 621 are respectively disposed in the image capturing circuit 610 and the temperature detecting circuit 620. Namely, in this embodiment, the processing circuit 630 only includes a wireless transmission circuit 631, an image signal processing circuit 632, a temperature signal processing circuit 633, and a memory 634. With such circuit arrangement, the hardware arrangement of the processing circuit 630 may be further simplified, and a hardware spatial utilization of the image capturing circuit 610 and the temperature detecting circuit 620 becomes more preferable.

In the following, a hardware arrangement where the image capturing driving circuit 611 and the temperature detection driving circuit 621 are respectively disposed in the image capturing circuit 610 and the temperature detecting circuit 620 is described with reference to FIG. 7.

Figure 7:
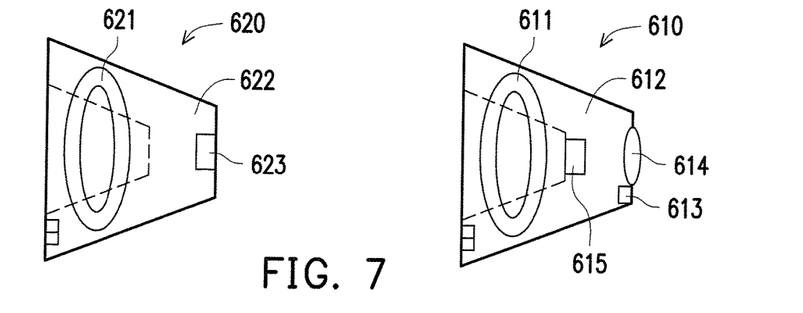
FIG. 7 is a schematic view illustrating a hardware arrangement of a functional circuit according the embodiment of FIG. 6.

Referring to FIG. 7, the image capturing circuit 610 of this embodiment includes the image capturing driving circuit 611, the embedded part 612, a light source 613, a lens set 614, and an image sensor 615.

In this embodiment, the hardware arrangement of the image capturing circuit 610 is similar to the image capturing circuit 320 of the third embodiment. A main difference therebetween is that in this embodiment, the annular image capturing driving circuit 611 is additionally disposed in an accommodating space of the embedded part 612, as shown in the right half of FIG. 7. Such arrangement allows a design where the image capturing driving circuit 611 is integrated with components such as the light source 613, the lens set 614, and the image sensor 615.

Also, the temperature detecting circuit 620 of this embodiment includes the temperature detection driving circuit 621, an embedded part 622, and an infrared sensor 623.

In this embodiment, the hardware arrangement of the temperature detecting circuit 620 is similar to the temperature detecting circuit 220 of the second embodiment. A main difference therebetween is that in this embodiment, the annular temperature detection driving circuit 621 is additionally disposed in an accommodating space of the embedded part 622, as shown in the left half of FIG. 7. Such arrangement allows a design where the temperature detection driving circuit 621 and the infrared sensor 623 are integrated together.

It should also be noted that the circuit arrangements and structural arrangements described in the embodiments of FIGS. 5-7 are applicable in the first to fourth embodiments. The invention does not intend to impose any limitation in this regard.

In view of the foregoing, the invention provides the hybrid detection apparatus integrating the temperature detecting function and the image capturing function. The user is able to conveniently expand the detection function of the already existing detection apparatus by using the single detection apparatus or disposing the additional functional circuit on the detection apparatus. Thus, the user does not need to separately use an endoscope and an ear thermometer to capture an image inside the body and detect the body temperature. Therefore, the invention creates a convenience when the user captures an image inside the body or detects the body temperature.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A hybrid detection apparatus, comprising:
a device body;
an image capturing circuit, adapted to be removably installed on the device body, wherein when the image capturing circuit is installed on the device body, the image capturing circuit is controlled to perform an image capturing function and generate an image signal accordingly; and
a temperature detecting circuit, adapted to be removably installed on the device body, wherein when the temperature detecting circuit is installed on the device body, the temperature detecting circuit is controlled to perform a temperature detecting function and generate a temperature signal accordingly,
wherein a second connection mechanism of the image capturing circuit and a third connection mechanism of the temperature detecting circuit are respectively fixed to a first connection mechanism of the device body by rotating joining, the device body is electrically connected to the second connection mechanism of the image capturing circuit through the first connection mechanism, the device body is electrically connected to the third connection mechanism of the temperature detecting circuit through the first connection mechanism, and the device body outputs a detection image based on the image signal and outputs a detection temperature based on the temperature signal,
wherein the device body comprises:
a holding part, having the first connection mechanism;
wherein the temperature detecting circuit comprises:
a first probe part, having the third connection mechanism corresponding to the holding part; and
an infrared sensor, disposed in the first probe part and adapted to sense infrared rays to generate the temperature signal accordingly.

2. The hybrid detection apparatus as claimed in claim 1, wherein the device body comprises:
a processing circuit, disposed in the holding part and adapted to perform signal processing on the image signal and the temperature signal, so as to generate the detection image and the detection temperature; and
a power circuit, disposed in the holding part and adapted to provide a working power required for operations of the image capturing circuit, the temperature detecting circuit, and the processing circuit.

3. The hybrid detection apparatus as claimed in claim 1, wherein the image capturing circuit comprises:
a second probe part, having the second connection mechanism corresponding to the holding part;
a light source, disposed on the second probe part;
a lens set, disposed on the second probe part to collect a light beam; and
an image sensor, disposed in the second probe part and on a light transmission path of the lens set to generate the image signal.

* * * * *